(12) United States Patent
Dussault et al.

(10) Patent No.: US 6,188,474 B1
(45) Date of Patent: Feb. 13, 2001

(54) OPTICAL SPECTROSCOPY SAMPLE CELL

(75) Inventors: Richard A. Dussault, Attleboro, MA (US); William R. Eppes, Great Diamond Island, ME (US); Ronald S. Scharlack, Brookline, MA (US)

(73) Assignee: Bayer Corporation, East Walpole, MA (US)

( * ) Notice: Under 35 U.S.C. 154(b), the term of this patent shall be extended for 0 days.

(21) Appl. No.: 09/310,552

(22) Filed: May 12, 1999

Related U.S. Application Data (60) Provisional application No. 60/085,253, filed on May 13, 1998.

(51) Int. Cl.$^7$ .............................. G01N 21/03; G01N 21/11
(52) U.S. Cl. ................................................................ 356/246
(58) Field of Search .................................... 356/413, 246, 356/440

(56) References Cited

U.S. PATENT DOCUMENTS

| | | | |
|---|---|---|---|
| 3,518,011 | 6/1970 | Rochte | 356/411 |
| 3,740,156 | * 6/1973 | Heigl et al. | 356/246 |
| 4,279,509 | * 7/1981 | Daffern | 356/246 |
| 4,643,570 | 2/1987 | Maächler et al. | 356/246 |
| 5,139,333 | 8/1992 | Reinhard | 356/246 |
| 5,268,736 | 12/1993 | Prather | 356/246 |
| 5,288,646 | 2/1994 | Lundsgaard et al. | 436/165 |
| 5,371,020 | 12/1994 | Frischauf | 436/165 |
| 5,430,542 | 7/1995 | Shepherd | 356/246 |

FOREIGN PATENT DOCUMENTS

| | | | |
|---|---|---|---|
| 93/06456 | 4/1993 | (WO) | G01N/21/03 |

OTHER PUBLICATIONS

Choat et al., Variable Path Length Flow–Through Cell for Spectrophotometry, *Anal. Chem.*, 58, (1986), pp. 2570–2571.

* cited by examiner

*Primary Examiner*—F. L. Evans
(74) *Attorney, Agent, or Firm*—Reed & Associates; Dianne E. Reed; Louis L. Wu (57) ABSTRACT

A sample cell for use in spectroscopy includes two cell portions that are mutually adjustable to enable a user to vary the cross sectional geometry of sample cell flow path thereof between at least two discrete configurations or positions. In a first position, the flow path may be provided with a relatively small cross-sectional area to provide a relatively small pathlength and generate high velocity fluid flow therethrough. The small pathlength enables use of relatively small sample volumes and facilitates optical measurement of samples, such as blood, which have relatively high optical density, absorbance or light scattering properties. In a second position, the flow path provides a larger cross-section adapted to permit larger agglomerations or clots to pass through the flow path to facilitate cleaning of the sample cell. The cell portions are maintained in slidable engagement with one another so that the adjustability of the flow path is accomplished by sliding movement of the cell portions relative to one another. In one embodiment, the cell portions are engaged along generally planar mating surfaces and the adjustability is accomplished by sliding the mating surfaces relative to one another. In another embodiment, the mating surfaces are superposed in spaced relation to one another, and the adjustability is accomplished by varying the distance therebetween.

19 Claims, 9 Drawing Sheets

FIG1A PRIORART

OPTICAL SPECTROSCOPY SAMPLE CELL

CROSS REFERENCE TO RELATED APPLICATIONS

This application claims the benefit of the filing date of U.S. Provisional Application Ser. No. 60/085,253, filed May 13, 1998, for OPTICAL SPECTROSCOPY SAMPLE CELL.

BACKGROUND OF THE INVENTION

1. Field of the Invention

This invention relates to spectrochemical determination of analyte content of a sample, and more particularly to a spectroscopy sample cell for analyte analysis of turbid media such as blood.

2. Background Information

Spectrochemical analysis is a broad field in which the composition and properties of materials in any phase, (liquids, solids, gases or plasmas) are determined from the electromagnetic spectra arising from interaction (for example, absorption, luminescence or emission) with energy. One aspect of spectrochemical analysis, known as spectroscopy, involves interaction of radiant energy with material of interest. The particular methods used to study such matter-radiation interactions define many sub-fields of spectroscopy. One field in particular is known as absorption spectroscopy, in which the optical absorption spectra of liquid substances is measured. The absorption spectra is the distribution of light attenuation (due to absorbance) as a function of light wavelength. In a simple spectrophotometer, the sample substance which is to be studied, usually a gas or liquid, is placed into a transparent container, also known as a cuvette or sample cell. Collimated light of a known wavelength, $\lambda$, i.e. ultraviolet, infrared, visible, etc., and intensity $I_o$, is incident on one side of the cuvette. A detector, which measures the intensity of the exiting light, I, is placed on the opposite side of the cuvette. The thickness of the sample is the distance d, that the light propagates through the sample. For a sample consisting of a single, homogenous substance with a concentration, c, the light transmitted through the sample will follow a well known relationship known as Beer's law which in part, states that the shorter the optical pathlength d, the less the absorption of light. If $\lambda$, $I_o$, I, d, c, are known, a quantity known as the extinction coefficient can be determined.

$$OD(\lambda) = c^* \epsilon(\lambda)^* d$$

Where:

$\epsilon(\lambda)$ is the extinction coefficient of the substance at wavelength $\lambda$;

$OD(\lambda)$ is the optical density of the sample at wavelength $\lambda$ (OD=-Log of the ratio: light transmitted (exiting)/light incident. ($-\text{Log}_{10} I/I_0$)

c is the concentration of the substance d is the pathlength or thickness of the sample through which the light propagates.

Beer's law is useful when one considers samples which are mixtures of several different substances, j, each with known extinction coefficients, $\epsilon_j$, and relative concentrations $c_j$. In such a case, the optical density of the sample is given by:

$$OD(\lambda) = \Sigma c_j^* \epsilon_j^*(\lambda)^* d$$

Inversely, if given a sample mixture's optical density spectra $OD(\lambda)$, and the extinction coefficients for each of the component substances, the unknown relative concentration of the component substances can be determined. Note, also, it is assumed that each of the component substances maintain the same extinction coefficients as when in a pure form, i.e. no chemical reactions occur that alter the extinction coefficients.

Thus, if the absorption spectra for a given substance is known, its presence and concentration in a sample may be determined.

Optimum optical pathlength depends on a variety of factors. In general, relatively small pathlengths are preferred as they enable use of smaller sample volumes and facilitate optical measurement of samples, such as blood, which have relatively high optical density, absorbance or light scattering properties. However, problems tend to occur when pathlengths as small as a few thousandths of an inch are used with whole blood samples. Unfiltered human blood may contain various formed elements (cell aggregates, protein/fibrin chains, synthetic fibers, clots, etc.), which when introduced into a narrow sample cell, can become lodged in the sample cell. These "clots" can obstruct the flow of wash fluids or subsequent samples, which can adversely affect the optical measurements. When high velocity air or liquid is forced through the sample cell, these clots can sometimes be dislodged. The introduction of a cleaning solution containing bleach or pepsin may also be effective in removing protein and fibrin from the sample cell. These cleaning solutions however, can only be used in systems which can tolerate exposure to such agents. In some cases, the sample cell may have to be replaced or disassembled and manually cleaned to remove such clots.

Optical measurements in whole blood can be further complicated by a number of issues. When red blood cells, the small "carriers" of hemoglobin (the light absorbing constituent to be measured), are suspending in serum, a light scattering (non isotropic) medium is produced. This is due to the differing indices of refraction of the red blood cell's intracellular fluid and the serum in which the cells are suspended. In such a case, Beer's law may not strictly apply and light scattering in the sample may result in significant errors in spectrophotometric measurements.

The degree of light scattering in whole blood is influenced by a number of normally occurring conditions such as variations in serum protein and lipid content, red cell morphology (size and shape), red cell concentration (number of red cells per unit volume), cell rouleaux formation, and red cell orientation.

Rouleaux formation occurs when a sample of whole blood is allowed to remain stationary, whereupon the red blood cells coalesce in an ordered fashion, forming "stacks" or "chains." This phenomenon, which is due, in part, to the bi-concave shape of the red cells and the colloids present in blood serum, significantly affects the optical properties of whole blood. Although some exceptions exist (e.g., certain animal bloods and rare variations in cell morphology/serum chemistry), this phenomenon occurs normally in most whole blood samples. The rate at which these rouleaux "chains" form is strongly dependent on red cell concentration.

Rouleaux formation is a reversible phenomenon. If the blood sample is mixed, stirred or made to flow through a channel of some type, resulting shear forces within the fluid will cause the rouleaux chains to disassemble and break up. Stopping the blood flow will allow, once again, the chains to form. If allowed to sit for extended periods of time, these rouleaux chains will settle and eventually result in the separation (stratification) of the blood cells and the blood serum.

Rouleaux formation alters the amount of light scatter observed in a given blood sample. It is important then, that a means of either accounting for or preventing the effect must be implemented. One way of preventing rouleaux chains from forming, is to force the blood to flow through a small channel. Shear forces, generated by differential velocities (velocity gradients) throughout the flow channel, if high enough, tend to prevent rouleaux chains from forming. A drawback of this approach however, is that use of a relatively small channel disadvantageously exacerbates the tendency for clogging or clotting, etc.

Another factor to be considered is whether or not the red cells are "oriented" during analyte measurement. Red cells tend to become oriented in a particular manner while flowing through narrow channels at relatively high velocity. A "normal" red blood cell is bi-concave (i.e. shaped much like a donut; thinner in the middle than at the edges) and measures approximately 8 microns ($8 \times 10^{-6}$ meters) across by 2 microns thick. A single normal red blood cell, if suspended in a carrier fluid experiencing relatively high velocity laminar flow, will be acted upon by the shear forces generated by the differential velocities in the fluid. Because of the cell's asymmetric shape, these forces will tend to orient the cells in some non-random fashion. This orientation of red blood cells occurs in mass (whole blood) flow, and is affected by the size and shape of the flow cell, particularly by use of flow cells having relatively small or restricted openings.

The amount of light transmission through a sample of whole blood where the red cells are randomly organized differs significantly from one in which the cells are oriented (i.e. non-randomly). This aspect of the red cells thus tends to further complicate spectroscopic analyte measurement in whole blood samples.

One attempt to overcome the aforementioned difficulties and provide accurate optical determination of analytes in blood samples has been embodied in instrumentation manufactured by Bayer Corporation of Medfield, Mass., known as the 800 Series analyzer. This instrumentation performs spectrophotometric measurements using lysed blood samples. The lysing process ruptures the red blood cell's membrane, releasing the intracellular fluid (primarily hemoglobin) into the surrounding serum. Lysing the red cells makes the sample relatively homogeneous and isotropic (i.e. essentially non-light scattering). Beer's law, as discussed above, then may be effectively applied to determine analyte concentration.

Ultrasonic energy provided by ultrasonic cell disrupters is typically utilized to lyse the red cells. A drawback of this approach is that these cell disrupters add cost, take up space, require maintenance and may generate bubbles in the sample which generate unpredictable light scatter induced errors. Also, the lysing process alters the sample's serum chemistry. Because of this, integrated instruments which combine lysed blood spectrophotometry with other sensor technologies that require whole blood for their measurements require additional sample volume for analysis. In these systems, a sample is aspirated into the instrument, then "split" into two segments to effectively isolate a portion of the sample for lysing and an other portion for whole blood analysis.

Thus, a need exists for an improved spectroscopy sample cell that avoids clogging, may be easily cleaned without special cleaning agents, is optimized for various operating modes including measurement, wash, fill, etc., is inexpensive and provides a stable mechanical environment for optical measurement repeatability.

SUMMARY OF THE INVENTION

According to an embodiment of this invention, a sample cell is provided for use in spectroscopic determination of an analyte in a fluid sample. The sample cell includes a sample path extending therethrough adapted for communicating fluid from an inlet, through a measurement zone to an outlet, the sample cell being selectively adjustable between a first position having a predetermined optical pathlength adapted for analyte measurement while the sample is in the measurement zone, and a second position having a predetermined other pathlength adapted for clearing the sample from the flow path.

The above and other features and advantages of this invention will be more readily apparent from a reading of the following detailed description of various aspects of the invention taken in conjunction with the accompanying drawings.

DETAILED DESCRIPTION OF THE PREFERRED EMBODIMENTS

Referring to the figures set forth in the accompanying Drawings, illustrative embodiments of the present invention will be described in detail hereinbelow. For clarity of exposition, like features shown in the accompanying Drawings shall be indicated with like reference numerals and similar features as shown in an alternate embodiment or to represent movement in the Drawings shall be indicated with similar reference numerals.

Briefly described, the present invention includes a sample cell 100 for use in spectroscopy, which includes two cell portions 48 and 52 that are mutually adjustable to enable a user to vary the cross-sectional geometry of sample cell flow path 16 thereof, between at least two discrete configurations or positions. In a first position, flow path 16 (FIG. 5A) may be provided with a relatively small cross-sectional area to provide a relatively small pathlength and to generate high velocity fluid flow therethrough. The small pathlength enables use of relatively small sample volumes and facilitates optical measurement of samples, such as blood, which have relatively high optical density, absorbance or light scattering properties. In a second position, flow path 16' (FIG. 5B) provides a larger cross-section to enable larger agglomerations or clots to pass through the flow path to facilitate cleaning of sample cell 100. Cell portions 48 and 52 are maintained in slidable, fluid tight engagement with one another so that the adjustability of flow path 16 is accomplished by sliding movement of cell portions 48 and 52 relative to one another. In one embodiment, the cell portions are engaged along generally planar mating surfaces 49 and 53, and the adjustability is accomplished by sliding the mating surfaces relative to one another. In another embodiment, mating surfaces 249 and 253 (FIG. 11) are superposed in spaced relation to one another, and the adjustability is accomplished by varying the distance therebetween.

Throughout this disclosure, the term "light" shall refer to electromagnetic radiation of a wavelength λ within the visible or near visible range, from approximately 100–30,000 nanometers, including far-ultraviolet, ultraviolet, visible, infrared and far-infrared radiation. Similarly, throughout this disclosure, the term "optical" shall be defined as pertaining to or utilizing light as defined herein.

Figure 1A:
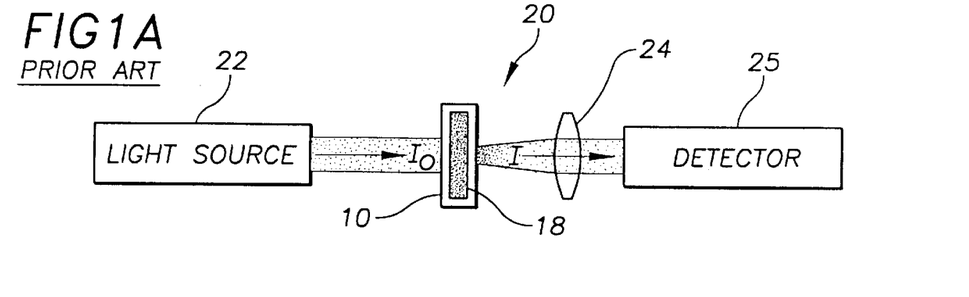
FIG. 1A is a schematic elevational side view of a sample cell and portions of a spectrophotometer of the prior art.
Figure 1B:
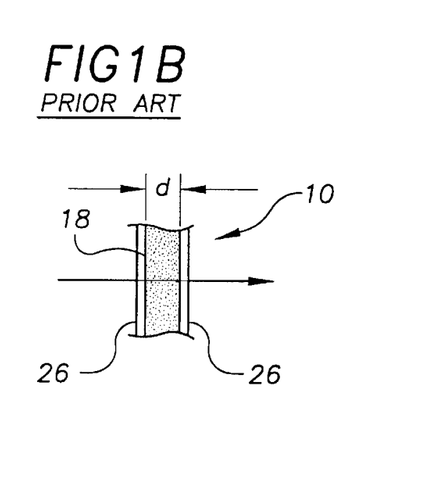
FIG. 1B is an enlarged view of a portion of the sample cell of FIG. 1A.
Figure 1C:
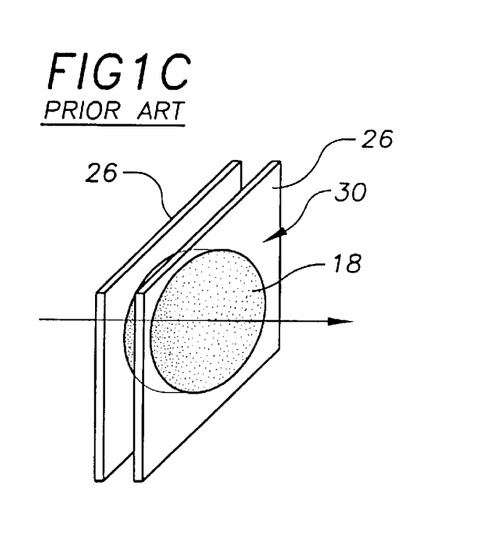
FIG. 1C is a perspective view of the sample cell of FIG. 1A.

Referring now to the drawings in detail, as shown in FIGS. 1A–1C, the primary purpose of sample cell or cuvette 10 is to confine the sample within a controlled geometry, while allowing for illumination and detection of the post interaction light intensity.

Turning to FIG. 1A in particular, in a simple spectrophotometer 20, a sample 18 is placed into a cuvette or sample cell 10. Collimated light of a known wavelength, λ, i.e. ultraviolet, infrared, visible, etc., and intensity $I_o$, is generated by a light source 22 and is incident on one side of the cuvette. Exiting light of intensity I typically passes through a lens 24 and is measured by a detector 25.

As shown in FIG. 1B, the thickness of sample 18 within sample cell 10 is the distance d that the light must propagate through. For a sample consisting of a single, homogeneous substance with a concentration, c, the light transmitted through the sample will tend to follow Beer's law as discussed hereinabove, to enable one to determine analyte presence and concentration within the sample.

Typically, as shown in FIG. 1C, two opposing sides of the cell consist of flat "windows" or panels 26 which are transparent to the wavelengths of light being used for the measurements. These windows are transparent at least in a predetermined optical measurement zone or area 30. As shown, measurement zone 30 preferably includes a substantially circular area as indicated by the disc-shaped portion of sample 18 shown in FIG. 1C.

Figure 2:
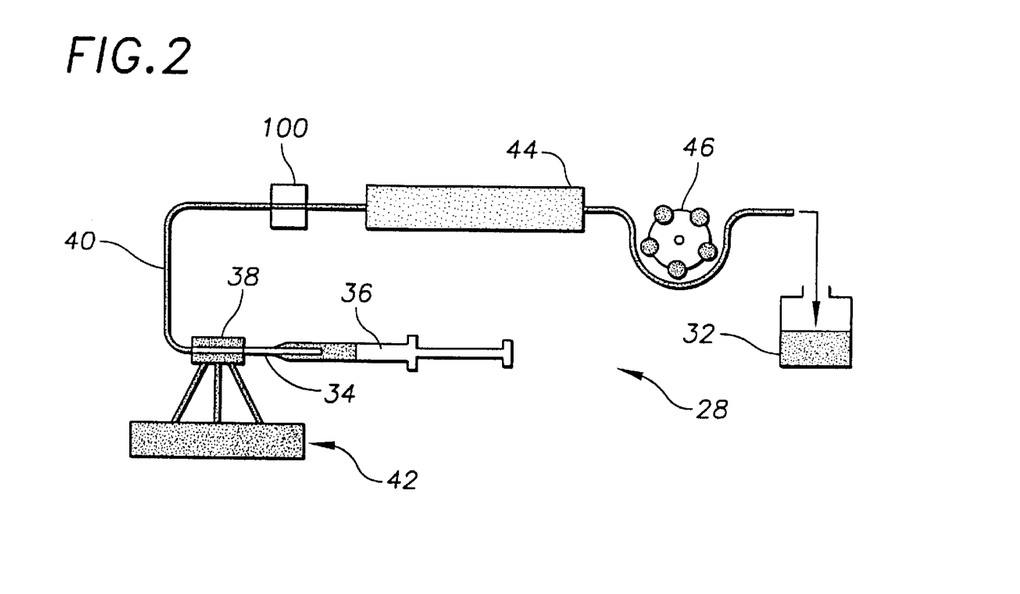
FIG. 2 is a schematic representation of a fluid delivery system adapted for use with a sample cell of the present invention.

Turning now to FIG. 2, the present invention enables a single, relatively simple, sample delivery system 28 to be utilized in integrated instrumentation (not shown) that combines whole blood spectrophotometry with other sensor technologies that utilize whole blood for their measurements. As used herein, the term "downstream" refers to the direction of fluid flow through delivery system 28, from a collection or storage device, to waste receptacle 32. The term "upstream" refers to a direction opposite the downstream direction. As shown, sample delivery system 28 includes a conventional sample aspirator probe 34 adapted for fluid communicating engagement at its upstream end with a conventional sample collection device or syringe 36 as shown. The aspirator probe communicates at its downstream end with a reagent valve 38, which in turn, communicates with a fluid path 40 defined, in part, by a conduit such as, for example, flexible tubing (not shown). Reagent valve 38 is also engaged with an array of calibration and wash fluid storage containers 42 as shown. The reagent valve is a device commonly known to those skilled in the art. Valve 38 operates in a conventional manner to selectively connect the calibration/wash fluids from container array 42, and a sample 18 disposed within syringe 36, to fluid path 40. An optical sample cell 100 of the present invention and various additional system sensors 44 are disposed within fluid path 40 downstream of reagent valve 38. System sensors 44 may include any number of individual sensors commonly known to those skilled in the art, such as for example, various electrochemical, optical, or electrical sensors including ion selective electrodes and luminescent sensors for such analytes as Calcium, Chloride, Oxygen, Carbon Dioxide, Glucose, pH, BUN, etc. A fluid pump 46 such as a conventional peristaltic pump is also disposed along the fluid path, preferably downstream of system sensors 44 as shown, and serves to draw the sample or calibration/wash fluids through delivery system 28. Fluid path 40 terminates at waste receptacle 32. Delivery system 28 serves to alternately move a sample 18 and calibration/wash fluid, through sample cell 100 for respective analyte measurement and calibration/wash sequences in a manner to be discussed hereinbelow.

Figure 3:
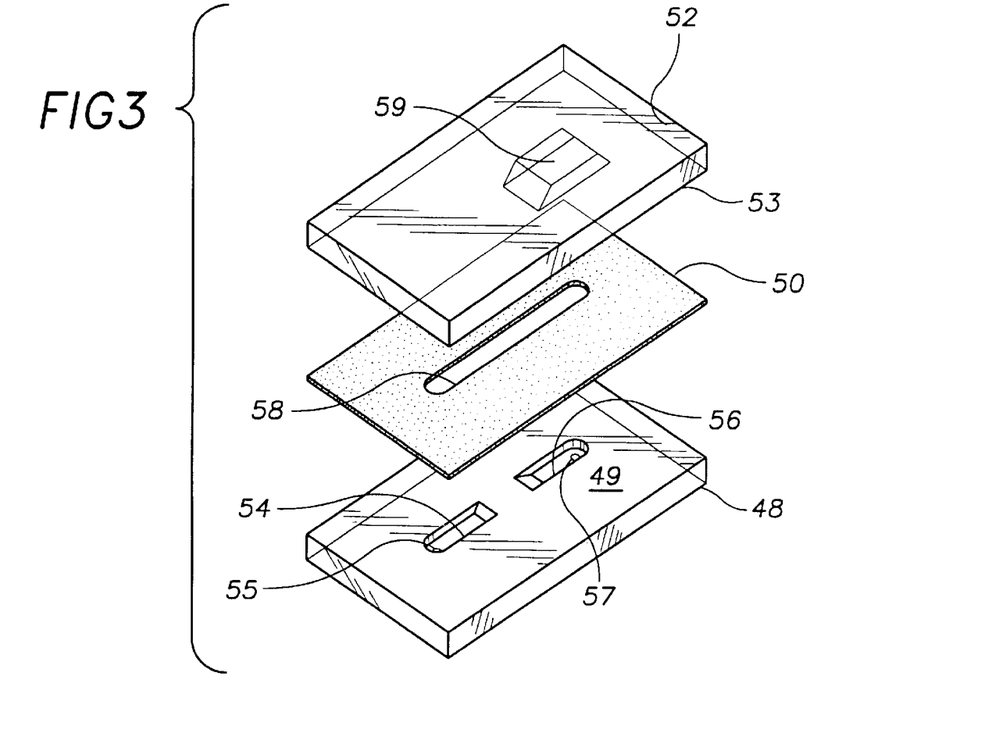
FIG. 3 is an exploded perspective view of a sample cell of the present invention.
Figure 4:
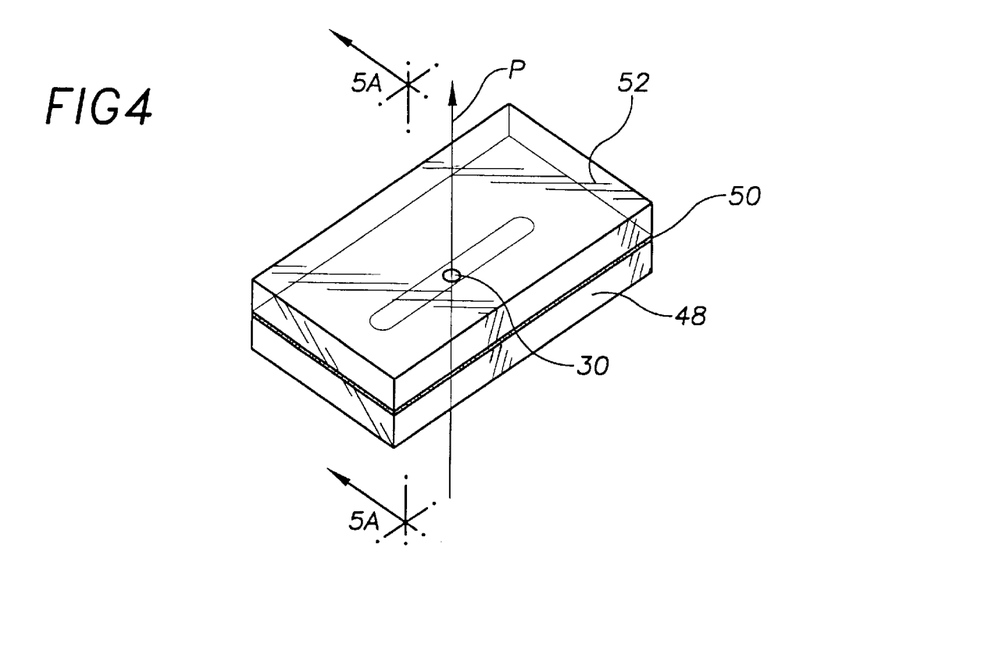
FIG. 4 is a perspective view of a sample cell of the present invention in a first position.
Figure 5A:
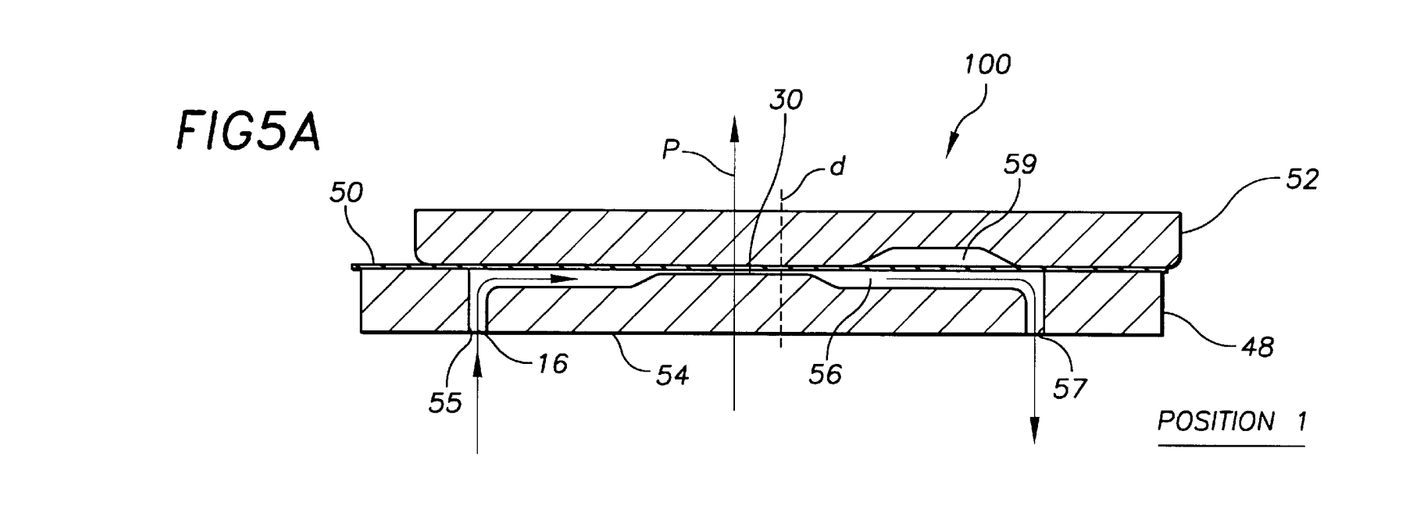
FIG. 5A is a cross-sectional elevational view taken along 5A—5A of FIG. 4.
Figure 5B:
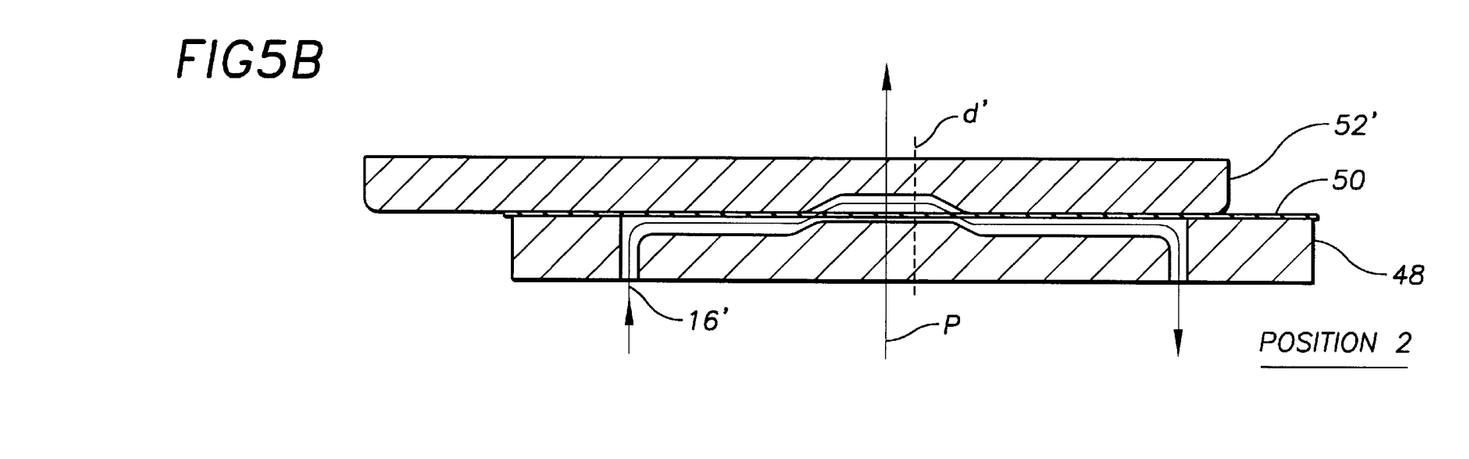
FIG. 5B is a view similar to that of FIG. 5A, of the sample cell of the present invention in a second position.

Referring to FIGS. 3–5, the present invention includes a sample cell 100 optimized for use in a spectrophotometer adapted to measure the concentration of various analytes within a moving or flowing sample of whole or lysed (human) blood. Sample cell 100 provides a means for optimizing flow to clear obstructions while also optimizing flow and optical pathlength for optical analyte measurement of blood (whole or lysed) or other samples of high optical density.

In one embodiment, as shown in FIG. 3, the sample cell includes three components, namely, a first or base portion 48, a fluid seal or gasket 50 and a second or cover portion 52. Base portion 48 includes concave entry and exit recesses 54 and 56, which terminate at entry and exit apertures 55 and 57, respectively. Gasket 50 includes an elongated cutout or slot 58 sized and shaped for superposed alignment with peripheries of both apertures 54 and 56 to comprise a sample cell flow path 16 (FIG. 5A) that extends from entry recess 54, through optical measurement zone 30, and to exit recess 56 when sample cell 100 is assembled as shown in FIG. 4. As also shown, mating surface 53 includes a hollowed out or substantially concave recess 59 that will be discussed in greater detail hereinbelow.

As shown in FIG. 4, components 48, 50 and 52 are sealably and slidably superimposed or stacked atop one another. In other words, base portion 48 and cover portion 52 are slidable relative to one another while a fluid-tight (i.e. gas and liquid tight) seal is maintained therebetween. As shown, gasket 50 may be compressed between mating surfaces 49 and 53 of portions 48 and 52, respectively, to facilitate this fluid-tight engagement. However, mating surfaces 49 and 53 may be provided with sufficient smoothness and uniformity to provide sufficient slidability and sealability without using gasket 50. Both portions 48 and 52 may be fabricated from any number of suitable materials, using a wide range of fabrication methods. For example, portions 48 and 52 may be fabricated from glass, crystal, quartz, sapphire or from a polymeric plastic material. In a preferred embodiment, portions 48 and 52 may be fabricated by injection molding a suitable thermoplastic material such as, for example, acrylic, polycarbonate, ultra high molecular weight or low density polyethylene, polyacrylonitrile, etc. The seal material may be an elastomer such as a hydrofluorocarbon elastomer sold under the trademark VITON available from DuPont Dow Elastomers Corporation. The choice of particular materials may be made based upon their mechanical, chemical and optical properties.

Base and cover portions 48, 50 are maintained in mating engagement as shown, by suitable support means (not shown). The distance between mating surfaces 49 and 53 at optical measurement zone 30, taken along optical path p orthogonal to the surfaces, defines optical pathlength d (FIG. 5A). Optical pathlength d may be predetermined by various means, such as by interposing a precision spacer or shim between base and cover portions 48 and 52. Alternatively, one or both mating surfaces 49 and 53 may be recessed within optical measurement zone 30 to establish the desired pathlength d. For example, surface 49 may be recessed in the optical measurement zone, as shown in FIG. 5A. One skilled in the art will recognize that such a recessed portion must be substantially planar and parallel to the opposite mating surface within measurement zone 30 to provide a relatively constant optical pathlength d.

Turning now to FIG. 5A, a portion of fluid flow path 40 (FIG. 2) as it extends through sample cell 100 is referred to as cell flow path 16. This path 16 includes entry aperture 55, recess aperture 54, measuring zone 30, exit recess 56, recess 59 and exit aperture 57. As shown, sample cell 100 is disposed in a first measurement or closed position, in which optimal pathlength d is maintained within optical measurement zone 30. Optimal pathlength d is determined by considering many factors. Several significant factors to be considered include the spectrophotometer's light source intensity, detection system characteristics such as available dynamic range, signal to noise ratio, resolution and sensitivity, as well as the sample substance's concentration and absorption properties (extinction coefficients) in the wavelength region of interest.

Moreover, red blood cell orientation is a function of cell concentration and morphology, sample flow velocity and flow channel geometry. It has been demonstrated experimentally that cell orientation may be controlled by adjusting these variables to generate relatively high shear force conditions. Advantageously, such high shear forces tend to promote red cell orientation. Optical pathlength d of the present invention is thus preferably predetermined to be sufficiently small so that when other flow conditions are controlled, the cells become oriented. This orientation serves to generate predictable light scatter properties during analyte measurement to facilitate accurate analyte measurement using samples 18 of whole blood.

Balancing these factors, sample cell 100 of the present invention may be provided with an optical pathlength d within a range of approximately 0.003 to 0.004 inches, preferably about 0.0035 inches. This relatively small optical pathlength d facilitates measurement of samples having high optical density, such as whole or lysed blood. Moreover, when sample cell 100 is disposed in this measurement position as shown, the transverse cross sectional area of flow path 16 throughout measurement zone 30 (defined herein as a cross-section taken parallel to optical path p and transverse to the downstream direction) is relatively small, preferably about 0.000175 square inches or less. This cross-sectional area tends to provide sufficient flow velocity to generate desired shear forces at a flow volume as low as approximately 7 microliters per second ($\mu$l/sec) to facilitate optical measurement of whole blood.

Referring to FIG. 5B, cover portion 52 has been slidably moved relative to base portion 48 and is thus indicated as 52'. As shown, sample cell 100 is disposed in its second or open position, in which recess 59 of cover portion 52 has been moved into optical measuring zone 30 of base portion 48. This movement is effected by any suitable means, such as an air cylinder or other pneumatic device, linear stepper/DC motor, solenoid, etc., or by manual manipulation. When in this open position, flow path 16', in the vicinity of measurement zone 30, is provided with a relatively large pathlength d' parallel to light path p, and a relatively large transverse cross-section.

Operation of sample cell 100 includes moving cover 52 into the measurement position as shown in FIG. 5A for analyte measurement. This provides a relatively small predetermined cross sectional area and optical pathlength d within the optical measurement zone 30 so that a sample 18 of blood passes through at relatively high red cell velocities and shear forces. As discussed hereinabove, these aspects tend to advantageously reduce rouleaux formation and promote red cell orientation in whole blood samples, while providing an optical pathlength d that facilitates optical measurement of high optical density samples such as whole or lysed blood.

After the sample has been analyzed, cover 52 is moved relative to base 48 into the second or wash position wherein wash fluid may be fed into the flow path to clean sample cell 100 for a subsequent sample 18. Many wash sequence options are facilitated by cell 100. For example, a wash sequence may begin with the sample cell in the closed measurement position. This would provide relatively high wash fluid velocity for cleaning the sample out of the optical measuring zone. The sample cell may then be switched into the open position during washing. Washing in the open position permits relatively large obstructions such as fibrin, clots, synthetic fibers, or other agglomerations, etc., to be freed. Moreover, sample cell 100 may be alternated back and forth between open and closed positions during the wash sequence if necessary to help dislodge obstructions.

Figure 6:
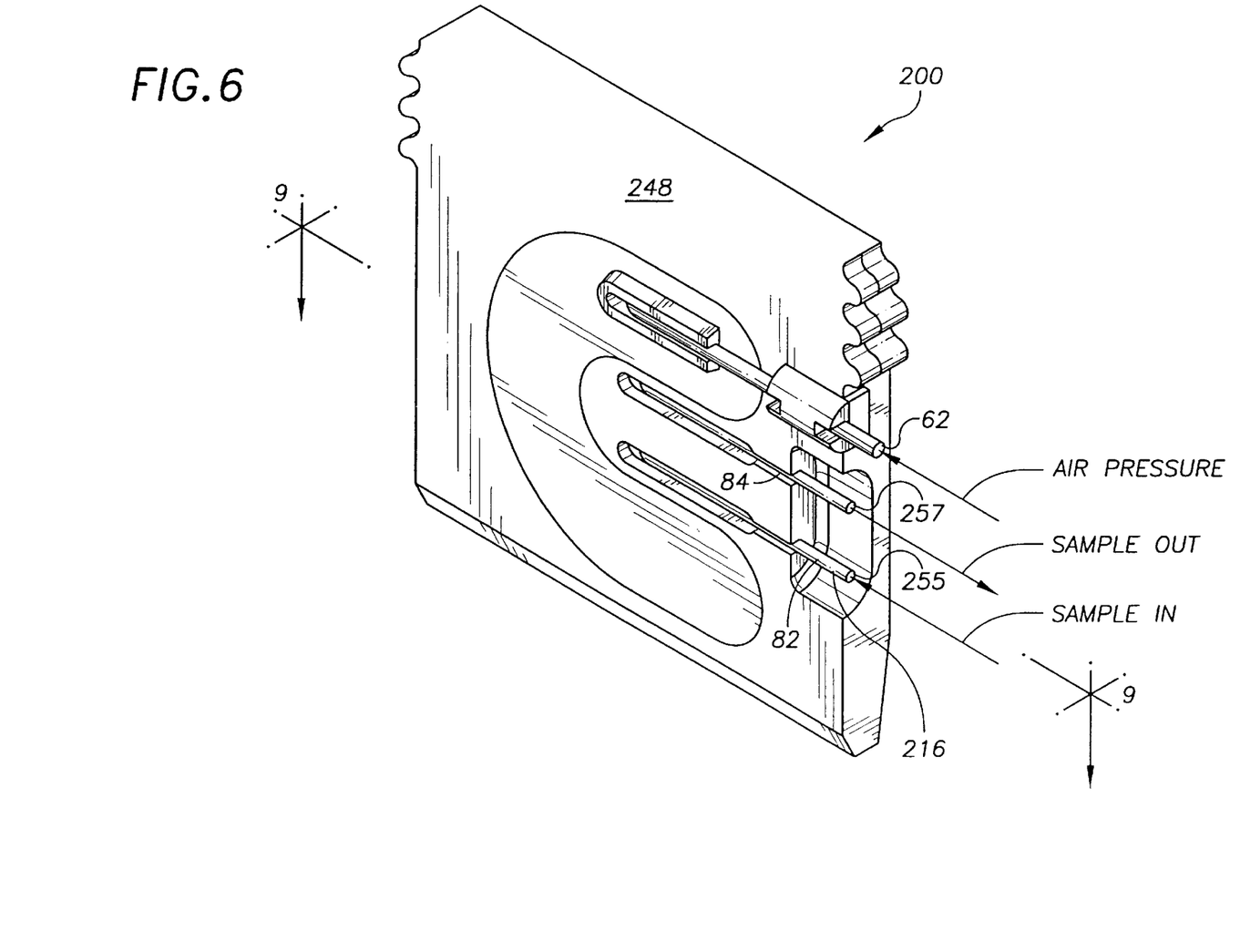
FIG. 6 is a perspective front view of an alternate embodiment of a sample cell of the present invention.

Turning now to FIG. 6, an alternate embodiment of the subject invention is shown as sample cell 200, which is in many respects similar or analogous to sample cell 100. Sample cell 200 includes a base or body portion 248. A tubular sample flow path 216 extends through base 248 and includes entry and exit portions 82 and 84 having sample entry and exit apertures 255 and 257, respectively. As shown, this sample cell is preferably a pneumatic device and includes a fluid inlet 62 which facilitates use of air or similar fluid pressure to actuate cell 200 between its open and closed positions, as will be discussed hereinafter.

Figure 7:
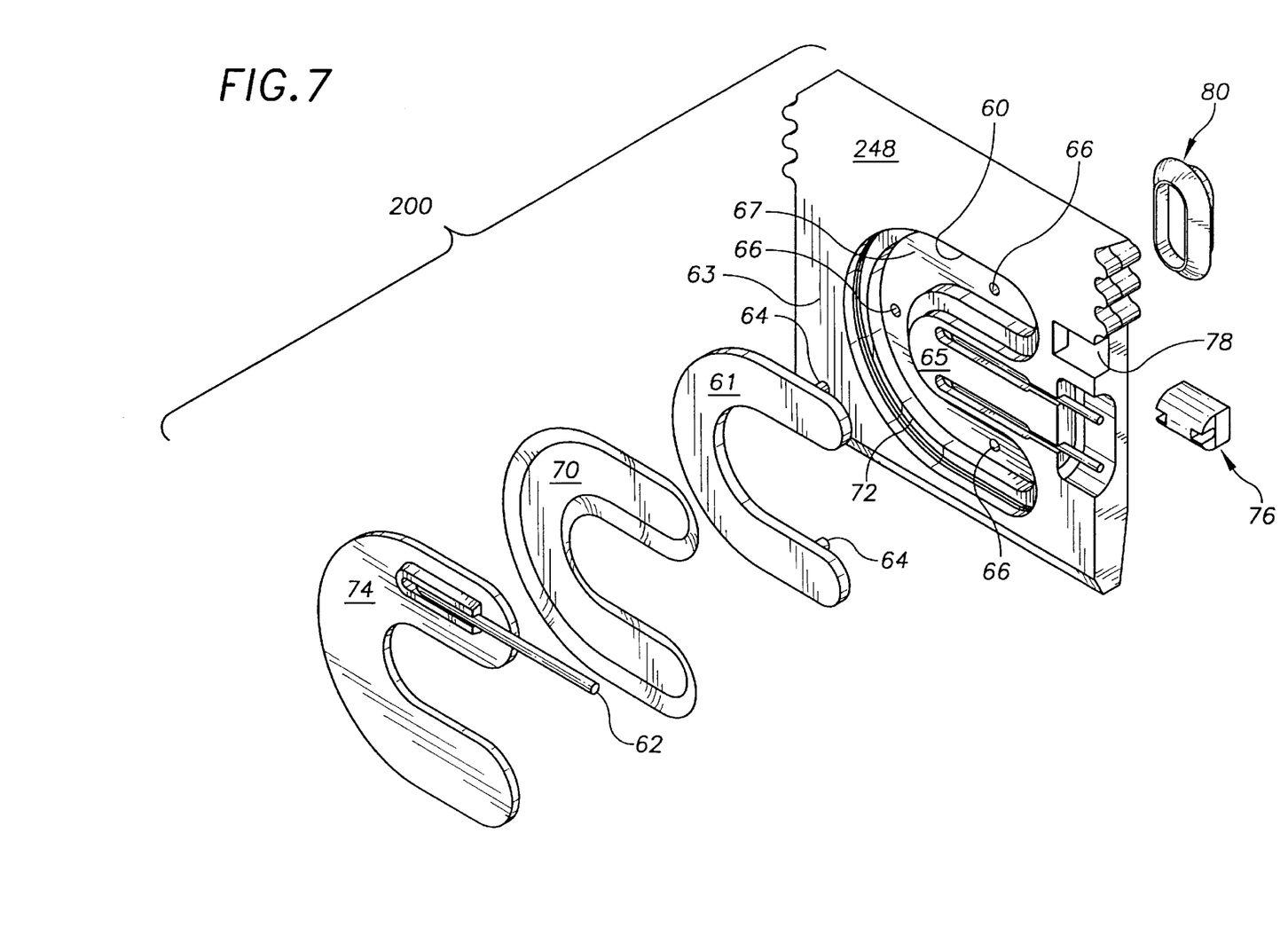
FIG. 7 is an exploded perspective front view of the sample cell of FIG. 6.

Referring to FIG. 7, sample cell 200 includes body 248 having a generally planar surface 63 and a cavity or trough 60 disposed therein. Cavity 60 is generally "U" or horseshoe shaped in the plane of surface 63 to substantially surround three sides of a central position or locus 65 of base 248. The cavity extends to a predetermined depth within base 248, terminating at a substantially planar bottom wall portion 67 disposed generally in parallel to mating surface 249 (FIG. 8) which will be discussed hereinbelow. Portion 67 includes a series of through holes 66 spaced generally equidistantly about locus 65. Each through hole 66 has a central axis a (FIG. 10) which preferably extends substantially orthogonally to bottom wall portion 67. A lifting shoe 61 is sized and shaped for slidable registration within cavity 60. A series of guidepins 64 are spaced along shoe 61 at predetermined locations to slidably and coaxially extend through corresponding through holes 66. Shoe 61 and cavity 60, including guidepins 64 and holes 66, are provided with predetermined dimensions sufficient to provide a predetermined range of motion of shoe 61 within cavity 60, in an axial direction defined by axis a, as will be discussed hereinbelow.

Sample cell 60 also includes a diaphragm 70 preferably fabricated from an elastomeric or rubber-like material, such as a polyvinyl elastomer. Diaphragm 70 is sealed in a fluid or airtight manner about its periphery to the periphery of cavity 60. In a preferred embodiment, the diaphragm is sealed to a peripheral ledge or lip 72 extending inwardly, generally orthogonally relative to the axial direction, from the periphery of cavity 60. A pneumatic chamber plug 74, which includes air inlet 62, is sized and shaped for receipt within cavity 60 in superposed relation with shoe 61 and diaphragm 70. Plug 74 is immovably fastened, in a gas tight manner to cavity 60, such as by ultrasonic welding or use of an adhesive or epoxy bond 77 (FIG. 10), so that plug 74 and diaphragm 70 form a gas tight pneumatic chamber 75 (FIG. 10) in fluid communication with air inlet 62. As also shown, a tube support 76, provided to support air inlet 62, is adapted for receipt within a corresponding receptacle 78 of base 248. A flexible elliptical gasket or elongated O-ring 80 is also provided, as best shown in FIG. 8.

Figure 8:
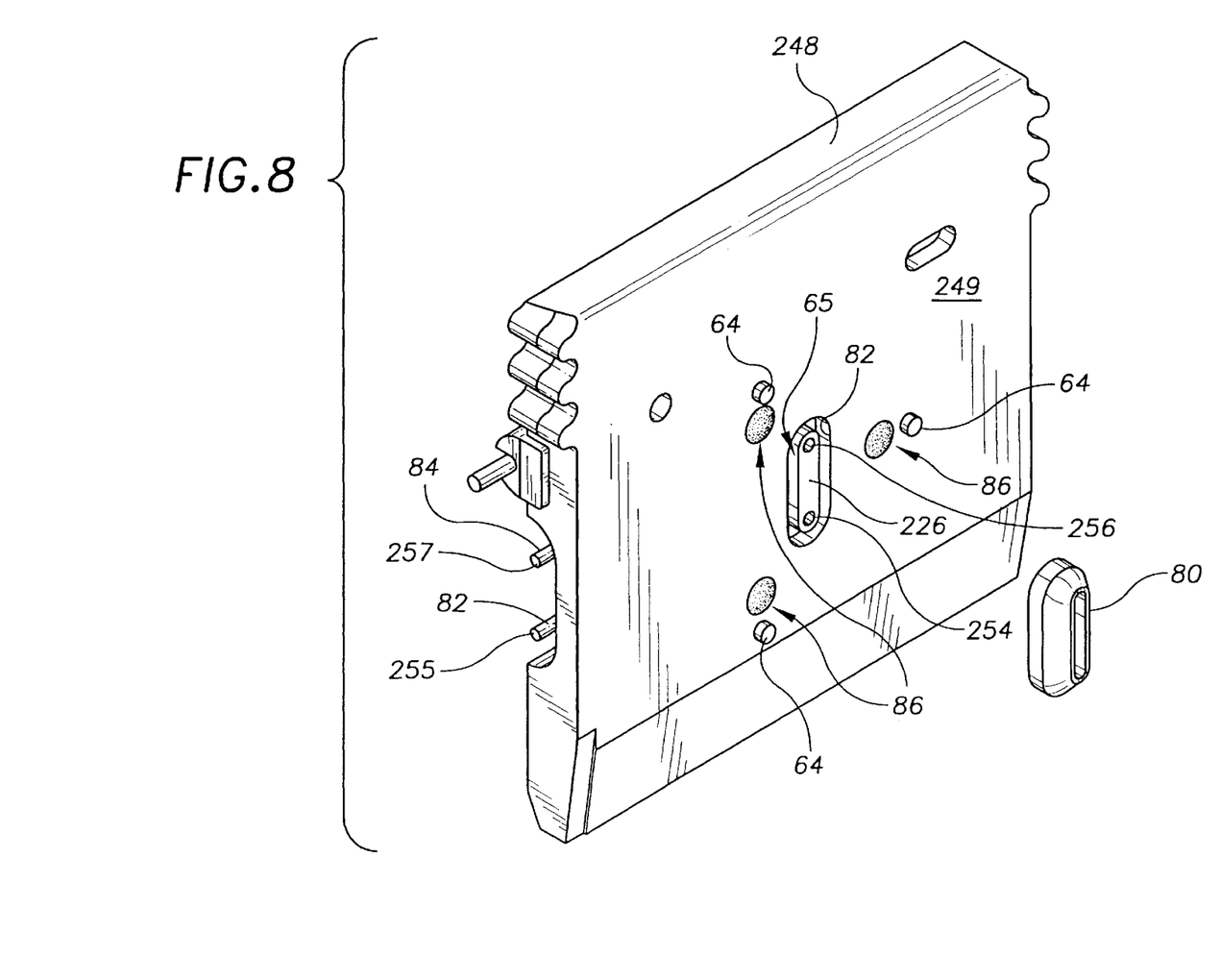
FIG. 8 is a partially exploded perspective back view of the sample cell of FIG. 7.
Figure 9:
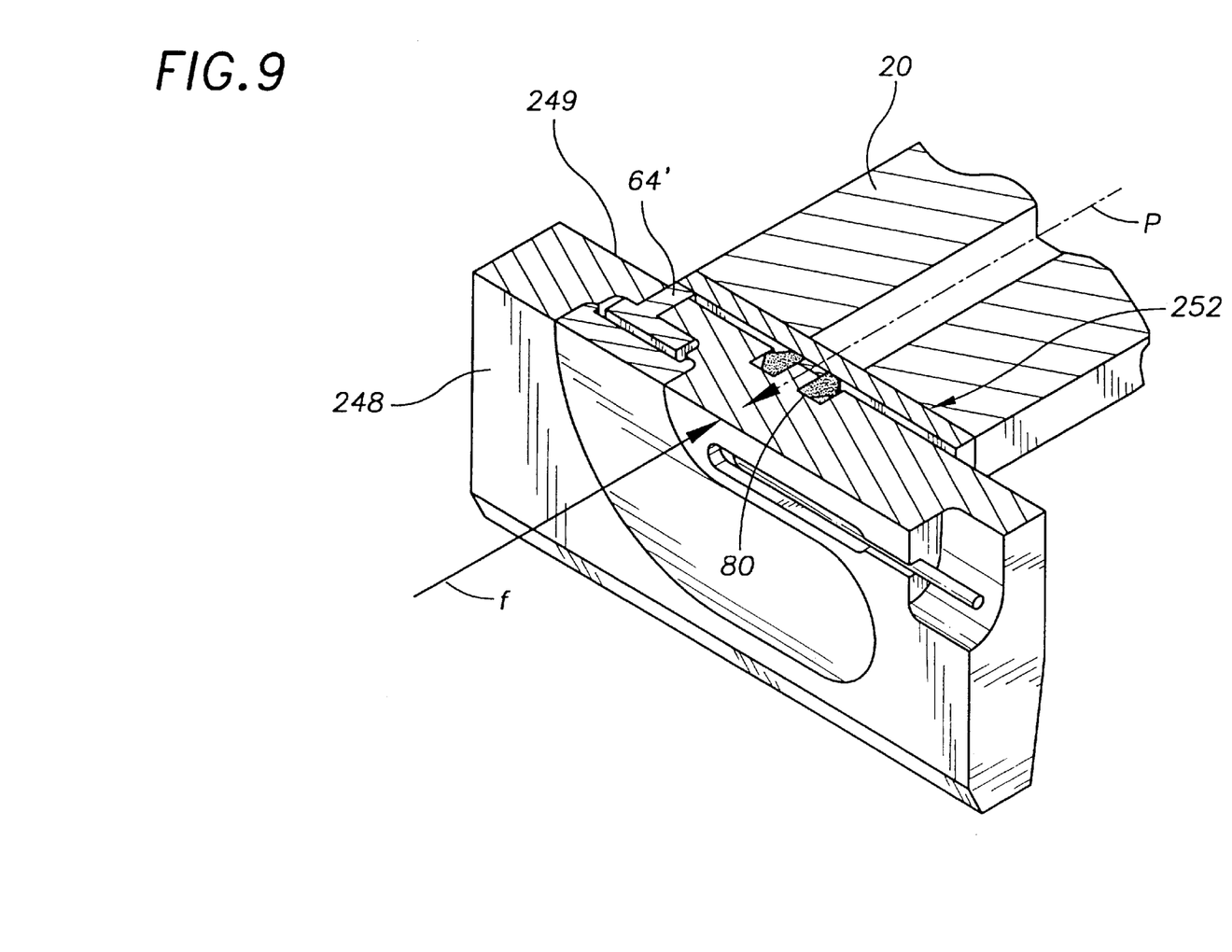
FIG. 9 is a cross-sectional view of the sample cell taken along 9—9 of FIG. 6, including a portion of instrumentation used therewith.
Figure 10:
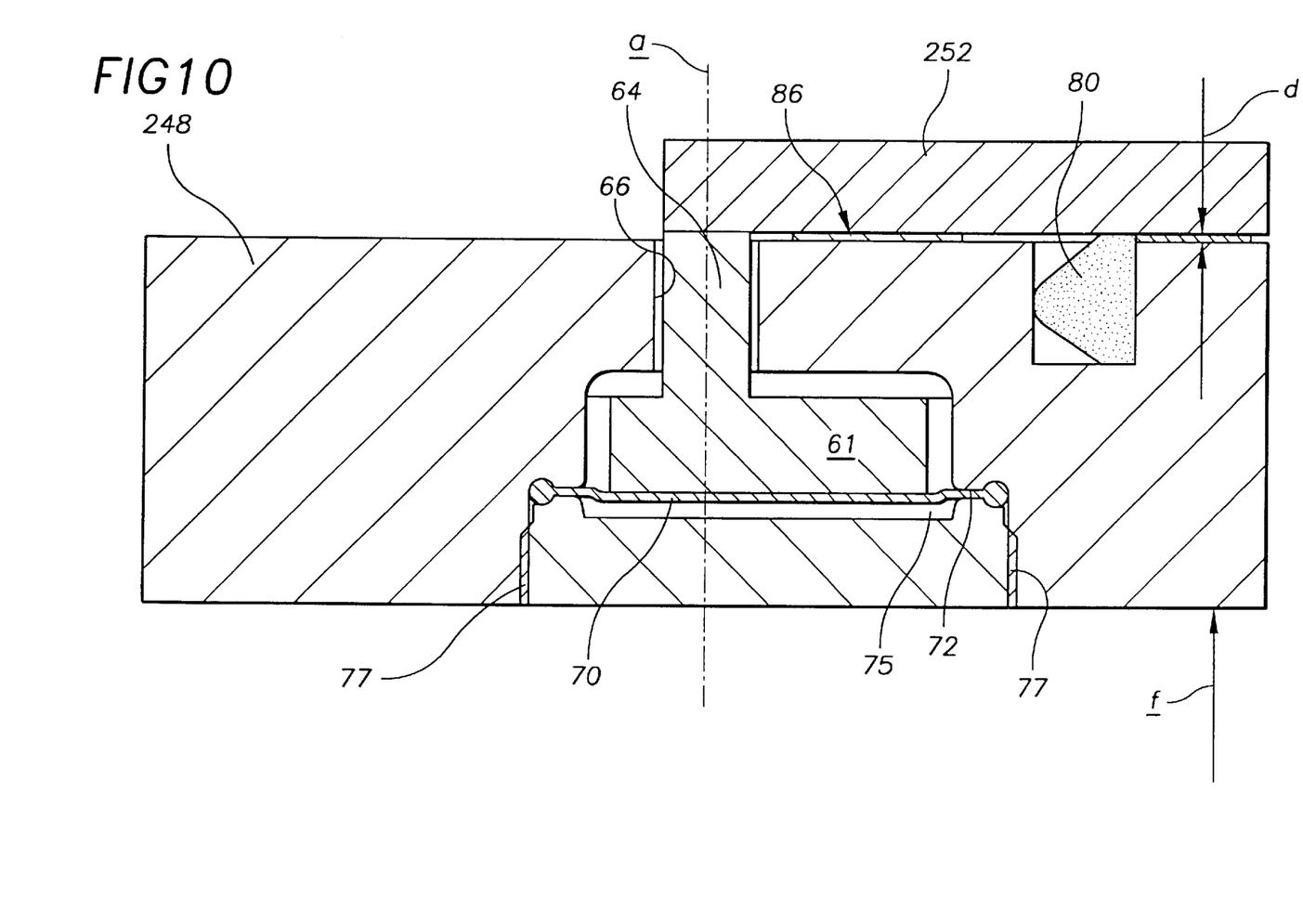
FIG. 10 is a top view of a portion of cross-sectioned sample cell of FIG. 9, on an enlarged scale, with the sample cell in a first position.
Figure 11:
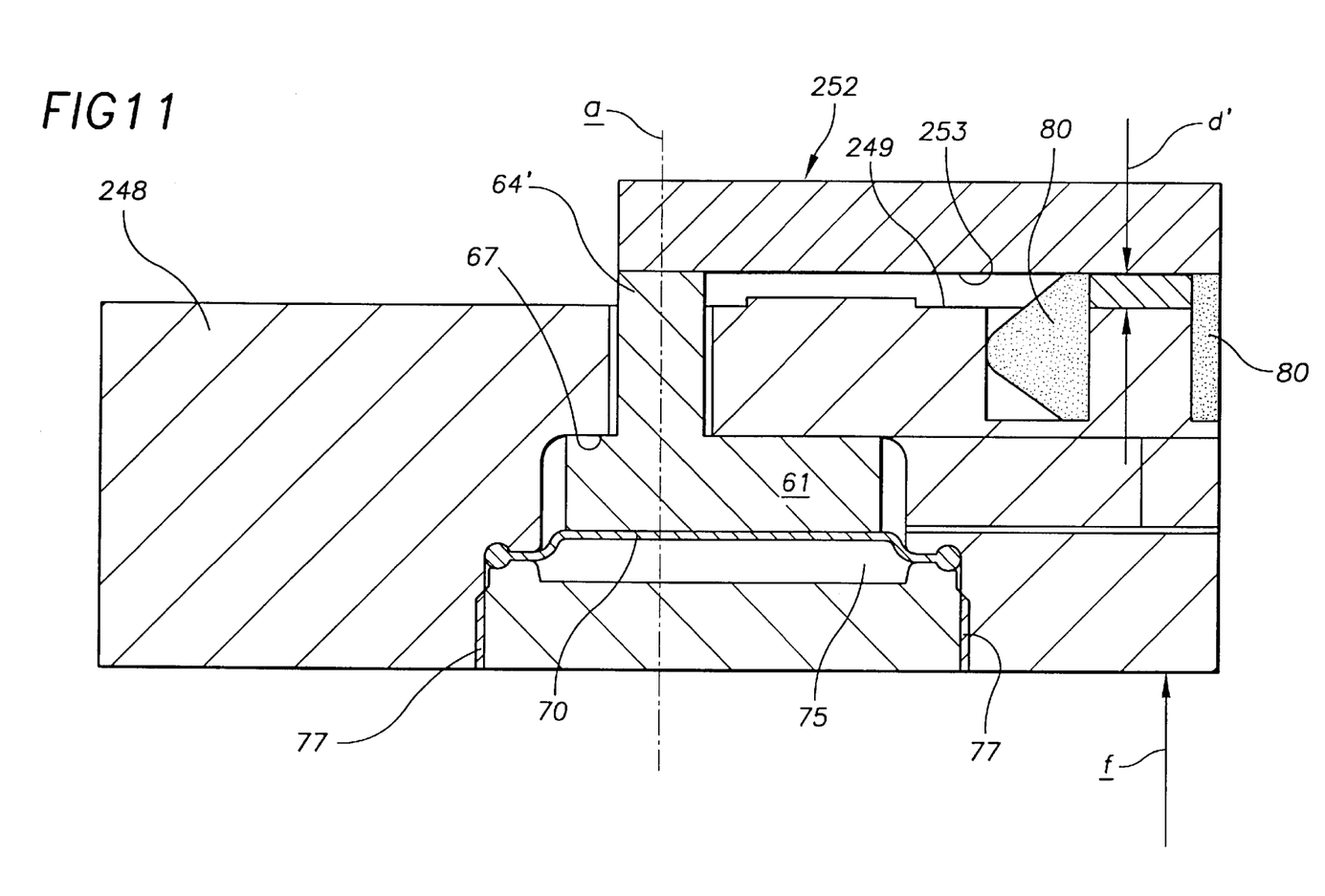
FIG. 11 is a view similar to that of FIG. 10, with the sample cell in a second position.

Turning now to FIG. 8, guidepins 64 are adapted to extend completely through holes 66 (FIG. 7) to protrude from substantially planar mating surface 249 of base 248 as shown, for connection to second portion or window 252 (FIGS. 9–11). A series of support pads 86 are disposed in spaced locations along surface 249, preferably proximate each guidepin 64. Entry and exit portions 82 and 84 of sample flow path 216 extend through base 248 and terminate at entry and exit recesses or openings 254 and 256 disposed in mating surface 249. As shown, openings 254 and 256 are disposed substantially at locus 65 between guidepins 64 and pads 86. Openings 254 and 256 are spaced a predetermined distance from one another, so that the portion of surface 249 disposed therebetween and between an elliptical channel 82 forms a window 226 in the optical measurement zone 30 of sample cell 200. As shown, elliptical channel 82 is recessed within surface 249 and encircles or surrounds openings 254 and 256. Gasket 80 is configured to be received within channel 82.

Referring now to FIG. 9, window 252 is shown engaged with one of the guidepins 64, while being supported on its opposite side by a portion of spectrophotometer 20. A predetermined compressive force f, provided by any convenient spring means (not shown) is applied to base 248 in a direction substantially orthogonal to mating surface 249 so that gasket 80 is sealingly compressed against window 252. The portions of window 252 and surface 249 enclosed by gasket 80 effectively form the sample chamber portion of flow path 216, including optical measurement zone 30, of sample cell 200.

Turning to FIG. 10, sample cell 200 is shown in its closed position, in which window 252 is substantially fully compressed against gasket 80 and engaged with support pads 86. Pneumatic chamber 75 is nominally at ambient pressure. Optical pathlength d is nominally the same as the thickness of pads 86. As discussed hereinabove with respect to sample cell 100, optical pathlength d may be approximately 0.003 to 0.004 inches, preferably approximately 0.0035 inches.

Referring now to FIG. 11, a p redetermined fluid (i.e. air) pressure has been applied to pneumatic chamber 75 through air inlet 62 which serves to expand the chamber and bias lifting shoe 61 and window 252 away from base 248 against the bias of force f. Lifting shoe 61 is moved by this expansion until the shoe engages or "bottoms out" against bottom wall portion 67. This engaged or bottomed out position defines predetermined pathlength d', which is optimally as large as approximately 0.015 to 0.025 inches. Sample cell is thus disposed in its open position. In this position, gasket 80, though decompressed relative to the closed position shown in FIG. 10, is still disposed in fluid sealing engagement with window 252 as shown.

Although preferred embodiments have been shown and described, several alternate embodiments of the sample cell of the present invention are envisioned. For example, sample cell 100 may be provided with multiple discrete optical pathlengths d such as by providing one or both surfaces 49 and 53 with a stepped profile. In this manner, a single sample cell of the present invention may be used to analyze samples having a relatively wide range of discrete absorption properties. Moreover, a further variation may include provision of a position in which a cell portion of known pathlength containing a "calibrator" may be disposed within the measurement zone 30. This calibrator may be a dye or an optical interference filter permanently disposed within a portion of one or both of the base 48 and cover 52. Such a feature may be useful when running diagnostics on instrument componentry such as light source 22 or other spectrophotometer components.

The sample cell of the present invention thus provides numerous benefits relative to the prior art. In particular, the cell is optimized for various operating modes, to enable optimized optical measurement of whole blood, while it also facilitates optimized washing, etc., to reduce difficulties associated with clogging. Moreover, the present invention substantially eliminates the need for a "hemolyzer" and the associated hydraulic components required to segment the sample into lysed and whole portions. This advantageously reduces system cost, size and tends to increase overall system hardware reliability. In addition, elimination of the lysing step advantageously maintains sample integrity. This permits measurements to be taken by other sensors, for which whole blood is required, on the same sample volume to effectively reduce the overall sample volume required for analysis. Still further, while the sample cell of the present invention facilitates optical measurement of whole blood samples, it also advantageously enables measurement of other samples having high optical density or light scattering properties such as lysed blood samples. The present invention thus provides the dual functionality of optical measurement of both lysed blood and whole blood samples.

The present invention may also substantially reduce the need for special cleaning agents to remove large protein formations which tend to occur when running many blood samples. In addition, clearing of such formations may be effected automatically, without manual user intervention.

Moreover, the present invention may be conveniently incorporated into an instrument which incorporates all measurement sensors, fluid handling components (valves, tubing, etc.) and calibration liquids, into a limited use, disposable "cartridge." Advantageously, such a configuration may provide the user with a system in which sensor and fluidic maintenance is not required. All system components that come in contact with the sample or reagent fluids may be disposed of when the cartridge expires.

Moreover, the predetermined dimensions of the first and second portions of the sample cells 100 and 200, provided by use of rigid components movable between predetermined positions to define optical pathlength d provides a stable mechanical environment for optical measurement repeatability. The sample cell of the present invention is also relatively inexpensive to manufacture.

Although the present invention has been described for use in absorption spectroscopy, one skilled in the art should recognize that the adjustable sample cell of the present invention may be utilized in conjunction with various other spectrochemical analysis techniques, including for example, luminescence or electromagnetic spectra emission measurement, without departing from the spirit and scope of the present invention.

Moreover, although sample cell 200 has been described as a pneumatic device that utilizes air or other fluid pressure to move first portion 248 relative to second portion 252, any suitable device or technique may be utilized to effect such movement, without departing from the spirit and scope of the present invention. For example, any suitable means, such as an air cylinder, linear actuator or stepper/DC motor, solenoid, etc., or even manual manipulation, may be utilized.

The foregoing description is intended primarily for purposes of illustration. Although the invention has been shown and described with respect to an exemplary embodiment thereof, it should be understood by those skilled in the art that the foregoing and various other changes, omissions, and additions in the form and detail thereof may be made therein without departing from the spirit and scope of the invention.

Having thus described the invention, what is claimed is:

1. A sample cell for use in spectroscopic determination of an analyte in a fluid sample, said sample cell comprising:
   a sample path extending between a first flow element and an opposing second flow element, wherein the sample path is adapted for communicating fluid from an inlet, through a measurement zone to an outlet, and the first flow element is slidable relative to the second flow element in a lateral manner to effect a selective adjustment between a first position having a predetermined optical pathlength adapted for analyte measurement while the sample is disposed in said measurement zone, and a second position having a predetermined other pathlength adapted for clearing the sample from said measurement zone.

2. The sample cell as set forth in claim 1, wherein said fluid sample comprises whole blood.

3. The sample cell as set forth in claim 1, wherein said fluid sample comprises lysed blood.

4. The sample cell as set forth in claim 1, wherein said selective adjustment selectively adjusts size ands shape of said sample path so that said predetermine optical pathlength is less than said predetermined other path length.

5. The sample cell as set forth in claim 1, wherein said selective adjustment selectively adjusts size and shape of said sample path so that at a predetermined sample flow volume, said first position provides a higher flow velocity than said second position.

6. The sample cell as set forth in claim 1, wherein said first flow element and said second flow element are slidably and sealably engaged along mating surface, said mating surfaces being slidable relative to one another to effect said selective adjustment.

7. The sample cell as set forth in claim 6, wherein said mating surfaces are substantially planar.

8. The sample cell as set forth in claim 7, wherein a gasket is disposed between said substantially planar mating surfaces.

9. The sample cell as set forth in claim 7, wherein said sample path comprises a substantially concave portion of at least one of said substantially planar mating surfaces, said concave portion adapted for selective movement out of and into said measurement zone during said selective adjustment between said first position and said second position.

10. A sample cell for use in spectroscopic determination of an analyte in a fluid sample, said sample cell comprising:
   a sample path extending therethrough adapted for communicating fluid from an inlet, through a measurement zone to an outlet, said sample cell being selectively adjustable between a first position having a predetermined optical pathlength adapted for analyte measurement while the sample is disposed in said measurement zone, and a second position having a predetermined other pathlength adapted for clearing the sample from said measurement zone; and
   a first flow element slidably and sealably engaged with a second flow element, said first element being slidable relative to said second element to effect said selective adjustment,
   wherein said first flow element and said second flow element comprise mating surfaces disposed in superimposed relation to one another, wherein distance between said mating surface is varied to effect said selective adjustment.

11. The sample cell as set forth in claim 10, wherein said mating surfaces are substantially planar.

12. The sample cell as set forth in claim 10, wherein said first flow element comprises at least one guidepin adapted for slidable engagement with at least one through-hole disposed in said second flow element.

13. The sample cell as set forth in claim 12, further comprising a resilient gasket disposed between said mating surfaces, said resilient gasket adapted to selectively expand and contract to maintain said mating surfaces in sealed engagement with one another during said selective adjustment between said first position and said second position.

14. The sample cell as set forth in claim 13, wherein said resilient gasket is adapted to bias said first element towards said first position, said sample cell further comprising biasing means adapted to bias said first element towards said second position against the bias of the resilient gasket.

15. The sample cell as set forth in claim 14, wherein said biasing means is pneumatic.

16. The sample cell as set forth in claim 15, wherein said biasing means comprises a diaphragm adapted to selectively apply pressure to slide said at least one guidepin through said at least one through-hole to move said mating surface of said first flow element away from said mating surface of said second flow element, wherein said sample cell is moved into said second position.

17. A sample cell for use in spectroscopic determination of an analyte in a fluid sample of lysed or whole blood, said sample cell comprising:
   a first flow element and a second flow element slidably and sealably engaged with one another along mating surfaces thereof, wherein said first flow element is adapted for selective adjustment relative to said second flow element between a first position and a second position;
   a sample path extending through said sample cell for communicating the fluid sample from an inlet, through a measurement zone, to an outlet;
   said sample path including a substantially concave portion of at least one of said mating surfaces, said concave portion adapted for selective movement into and out of said measurement zone during said selective adjustment, wherein said measurement zone has a predetermined optical pathlength adapted for analyte measurement when said sample cell is disposed in said first position, and an other pathlength greater than said optical pathlength when said sample cell is disposed in said second position, for clearing the sample from said measurement zone.

18. A method for spectroscopically determining presence of an analyte in a fluid sample, said method comprising the steps of:

(a) providing a sample cell having a sample path extending between a first flow element and an opposing second flow element, wherein the sample path is adapted for communicating fluid from an inlet, through a measurement zone to an outlet, and the first flow element is slidable relative to the second flow element in an lateral manner to effect an selective adjustment between a first position having a predetermined optical pathlength adapted for analyte measurement while the sample is disposed in said measurement zone, and a second position having a predetermined other pathlength adapted for clearing the sample from said measurement zone;

(b) adjusting the sample cell to the first position;

(c) inserting a fluid sample into the measurement zone;

(d) spectroscopically determining presence of the analyte in the sample;

(e) adjusting the sample cell to the second position; and (f) clearing the sample from the measurement zone.

19. The method as set forth in claim 18, wherein the selective adjustment selectively adjusts size and shape of the flow path so that the predetermined optical pathlength is less than the predetermined other pathlength, so that at a predetermined flow volume, the first position provides a higher flow velocity than the second position.

* * * * *